United States Patent [19]

Aoyama et al.

[11] Patent Number: 5,780,257
[45] Date of Patent: Jul. 14, 1998

[54] METHOD AND REAGENT FOR DETECTING PEROXIDASE OR HYDROGEN PEROXIDE

[75] Inventors: Masaaki Aoyama, Yamagata, Japan; Masanobu Shiga, Rockville, Md.

[73] Assignees: Yamagata Technopolis Foundation; JEOL Ltd., both of Japan

[21] Appl. No.: 683,148

[22] Filed: Jul. 18, 1996

[51] Int. Cl.[6] .............................. C12Q 1/28; C12Q 1/26; G01N 33/53; G01N 24/00
[52] U.S. Cl. .............................. 435/28; 435/25; 435/968; 423/582; 423/584; 564/300; 436/173
[58] Field of Search .............................. 435/6, 7, 28, 25, 435/968; 423/582, 584; 564/300; 436/173

[56] References Cited

U.S. PATENT DOCUMENTS

| | | | |
|---|---|---|---|
| 4,828,983 | 5/1989 | McClune | 435/7 |
| 5,372,931 | 12/1994 | Friedman et al. | 435/6 |

OTHER PUBLICATIONS

Fischer et al., "Direct Electron Spin Resonance Detection of Free Radical Intermediates During The Peroxidase Catalyzed Oxidation of Phenacetin Metabolites," Chemico–Biological Interactions 1986, 60, 115–127, Nov. 1986.

Ross et al., "The Generation and Subsequent Fate of Glutathonyl Radicals in Biological Systems," J. Biol. Chem. 1985, 260, 15028–15032, Dec. 5, 1985.

Thorpe, Gary H. G., et al., "Enhancement of the Horseradish Peroxidate–Catalyzed Chemiluminescent Oxidation of Cyclic Diacyl Hydrazides by 6–Hydroxybenzothiazoles", Analytical Biochemistry 145, 96–100 (1985), pp. 96–100.

Klebanoff, S. J., "An Effect of Thyroxine and Related Compounds on the Oxidation of Certain Hydrogen Donors by the Peroxidase System", Journal of Biological Chemistry, vol. 234, No. 9, Sep. 1959, pp. 2437–2442.

Toshiyuki Ohnishi et al., "One–Electron–Transfer Reactions In Biochemical Systems", Biochim. Biophys. Acta, 172 (1969) pp. 357–369.

Primary Examiner—Louise Leary
Attorney, Agent, or Firm—Webb Ziesenheim Bruening Logsdon Orkin & Hanson, P.C.

[57] ABSTRACT

Method for detecting peroxidase or hydrogen peroxide with high sensitivity. Both peroxidase and hydrogen peroxide are prepared such that one of them is overabundant to the other. Phenoxy radicals are produced from a p-substituted phenol compound by the action of peroxidase in the presence of hydrogen peroxide. The free radicals are trapped by a hydroxy amine compound, and stable radical species are produced. Electron spin resonances of the stable radical species are measured.

8 Claims, 3 Drawing Sheets

METHOD AND REAGENT FOR DETECTING PEROXIDASE OR HYDROGEN PEROXIDE

FIELD OF THE INVENTION

The present invention relates to a method of detecting peroxidase or hydrogen peroxide. The invention also relates to reagents used for the detection of peroxidase (POD) or hydrogen peroxide ($H_2O_2$).

BACKGROUND OF THE INVENTION

Chemiluminescence using chemical reagents, such as luminol, is well known as a method for detecting peroxidase. A method using p-substituted phenol derivatives has been proposed in order to improve the sensitivity of the measurement utilizing chemiluminescence. For example, it has been reported that chemiluminescence due to luminol-$H_2O_2$-POD is intensified by p-iodophenol (Kricka, et al., *Anal. Biochem.*, 145, 96, 1985). Luminol is used as a monoanion complex of luminol in an aqueous solution and is changed to thiazasemiquinone radical by an oxidative reaction of a p-substituted phenol compound. The thiazasemiquinone radical is finally changed to 3-amino phthalic acid via some intermediates. The chemiluminescence occurs at the final step in the reaction. The iodophenol (iodophenol radicals) reacts with the luminol and promotes the generation of thiazasemiquinone radicals. An immunity-measuring reagent named "Amerlite" used for this principle is available from Nippon Kodak Diagnosis Techcs Co., Ltd., Japan.

It has been reported that addition of p-methoxyphenol to ascorbic acid-$H_2O_2$-POD enhances generation of ascorbic radicals (Chance, B., *Arch. Biochem. Biophys.*, 41, 389, 1952). Similar enhancing reactions can be produced by using p-cresol (Ohnishi, T. et al., *Biochem. Biophys. Acta*, 172, 357, 1969) or thyroxine or its analogues (Klebanoff, S. J., *J. Biol. Chem.*, 234, pp. 2437–2442, 1972).

A p-substituted phenol derivative induces enhancement of luminol luminescence and of generation of ascorbic radicals, therefore, it is useful as an enhancer in detecting peroxidase. In the reaction, phenoxy radicals produced by peroxidase act on luminol and on ascorbic acid, causing a one-electron pullout (oxidation) reaction. However, even if a method making use of such intensified luminescence or radical amplification is adopted, peroxidase is not detected with sufficient sensitivity. Especially where peroxidase is detected utilizing radical amplification, the minimum concentration of detection is about $10^{-3}$ units/ml. It is obvious that the sensitivity is insufficient for a reagent for enzymatic immunoassay.

SUMMARY OF THE INVENTION

It is an object of the present invention to provide a novel method for detecting peroxidase or hydrogen peroxide with high sensitivity.

It is another object of the invention to provide reagents permitting high-sensitivity detection of peroxidase or hydrogen peroxide.

Where a p-substituted phenol derivative is used as an enhancer, the achieved enhanced efficiency of the sensitivity might depend on the life of phenoxy radicals produced by the action of peroxidase. Accordingly, applicants have understood that the above-described method is unable to accomplish a great sensitivity improvement because neither luminol radicals (or reaction intermediates) nor ascorbic radicals (or final products) are stable radicals. The applicants have earnestly searched for an enhancer for producing stable phenoxy radicals and for means for converting phenoxy radicals into other stable radical species producing strong signals.

As a result, it has been discovered that where phenoxy radicals produced from a p-substituted phenol derivative that is an enhancer are oxidized by a hydroxy amine derivative, stable radical species producing strong ESR signals are generated. Also, it has been found that peroxidase can be detected with quite high sensitivity if a p-acetamide phenol derivative is utilized as an enhancer in employing the above-described hydroxy amine derivative. Furthermore, it has been found that hydrogen peroxide can be detected by causing an excessive amount of peroxidase to be present in the same reaction system. The present invention has been made, based on the above-described findings.

DETAILED DESCRIPTION OF THE INVENTION

Figure 1A:
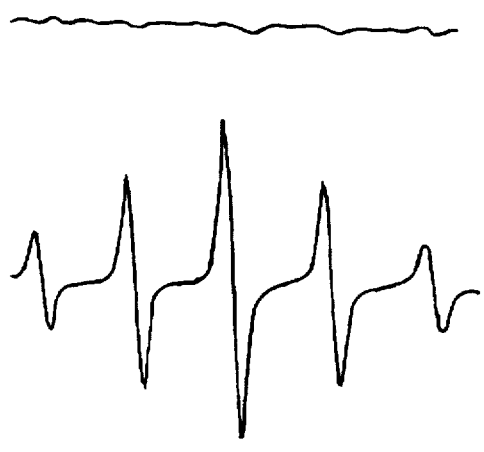
FIG. 1(a) is an ESR spectrum of a hydroxy amine compound, consisting of carboxy-PTIOH, oxidized by phenoxy radicals, and in which the upper line indicates the ESR signal under a blank condition.

The present invention includes a method for detecting peroxidase or hydrogen peroxide in accordance with the present invention comprises the steps of: preparing peroxidase and hydrogen peroxide such that one of them is excessive for the other; producing phenoxy radicals from a p-substituted phenol compound by the action of the peroxidase in the presence of the hydrogen peroxide; oxidizing the phenoxy radicals by a hydroxy amine compound to produce stable radicals; and measuring electron spin resonances of the stable radical species.

One preferred embodiment of the invention is based on the above method and characterized in that the p-substituted phenol compound is 4-acetamide phenol derivative where the p-substituted phenol compound is given by

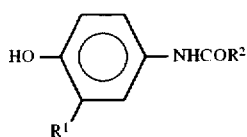

where $R^1$ is a hydrogen atom or $C_{1-6}$ alkyl group, $R^2$ is $C_{1-6}$ alkyl group, carboxyl, or $C_{1-6}$ alkoxy carbonyl group. Alternatively, the p-substituted phenol compounds are selected from the group consisting of 4-methoxyphenol, 4-ethoxyphenol, 4-iodophenol, 3-(4-hydroxyphenyl) propionic acid (HPPA), 4-hydroxyphenylacetic acid, 4-hydroxyhippuric acid, p-cresol and tyramine.

In another embodiment of the invention, a reagent for detection of peroxidase or hydrogen peroxide consists of a hydroxy amine compound capable of trapping electrons of phenoxy radicals produced by the enzymatic reaction of peroxidase under the presence of peroxidase and hydrogen peroxide and, preferably, the aforementioned 4-acetamide phenol derivative and of producing stable radical species. Also, a hydroxyamine compound is offered that is a phenoxy radical-trapping reagent capable of trapping electrons of phenoxy radicals produced by the action of peroxidase under the presence of peroxidase and hydrogen peroxide and, preferably, the aforementioned 4-acetamide phenol derivative and of producing stable radical species.

The hydroxy amine compound used in the method according to the present invention is a compound reacting as a reagent for detection of peroxidase or hydrogen peroxide. This compound traps phenoxy radicals produced by the action of peroxidase under the presence of hydrogen peroxide and a p-substituted phenol compound. As a result, stable radical species are generated. It is to be noted that the present invention does not stick to any certain theory. These hydroxy amine compounds trap phenoxy radicals and give rise to stable nitroxide (NO) radical species. These stable radical species can be quantitatively detected by an electron spin resonance (ESR) spectrometer. In this way, peroxidase or hydrogen peroxide can be detected with quite high sensitivity. Detections and measurements referred to herein embrace qualitative analysis, quantitative analysis and every kind of detection.

Any kind of hydroxy amine compound can be used as the above-described hydroxy amine compound used as a reagent for detection of peroxidase or hydrogen peroxide, as long as the compound can trap electrons of phenoxy radicals and produce stable radical specimens. It would be easy for those skilled in the art to make a decision according to the method described in the body of the present specification as to whether the hydroxy amine compound has characteristics preferable for the method according to the invention. Generally, stability of radical species can be judged from their lives, aging characteristics of ESR signal intensities or other factors.

Preferred reagents used for detection of peroxidase or hydrogen peroxide can be hydroxy amine compounds which have the above-described characteristics and are obtained by reducing nitroxide (nitron) compounds that can be used as free radical spin-labeling agents. Nitroxide compounds which can be used as raw materials include: TEMPO (2,2,6,6-tetramethyl-1-piperidinyloxy), its derivatives, PROXYL (2,2,5,5-tetramethylpyrrolidinyloxy), its derivatives, carboxy-PTIO [2-(4-carboxyphenyl)-4,4,5,5-tetramethylimidazoline-1-oxyl-3-oxide), its derivatives, DOXYL (4,4-dimethyl-3-oxazolinyloxy), and its derivatives. All of these compounds are commercially available (see, for example, a catalog of Sigma Corporation, 1995 edition, 1943, "SPIN LABELS AND SPIN TRAPS") and are easy to obtain. Furthermore, nitroxide-based spin labeling agents as described, for example, by Tokuko Watanabe in the summary of Dhojin News, No. 1, "Application of Spin Labeling to Biopolymers", 1976, can be used as nitroxide compounds.

Hydroxy amine compounds which can be preferably used in the novel method are given by

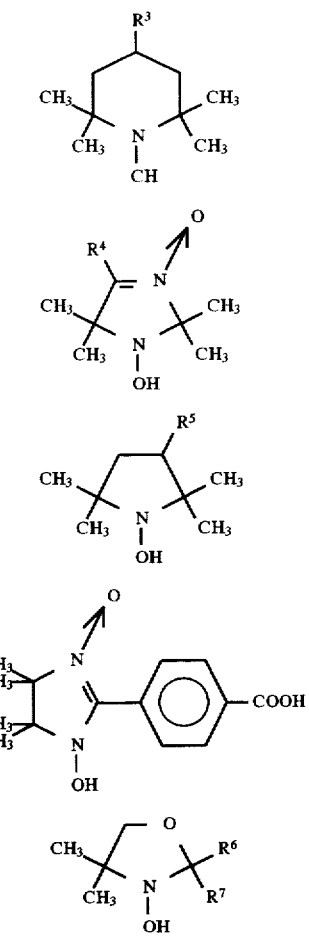

where $R^3$ is a hydroxyl group, a substituted or non-substituted amino group (preferably non-substituted amino group), carboxyl, or $C_{1-6}$ alkoxy carbonyl group; $R^4$ is a hydrogen atom, $C_{1-6}$ alkyl group (preferably methyl group), or hydrazid group; $R^5$ is hydroxyl group, a substituted or non-substituted amino group (preferably $C_{1-6}$ alkyl carbonyl-substituted amino group or non-substituted amino group), carboxyl, or substituted or non-substituted carbamoyl (preferably non-substituted carbamoyl); $R^6$ is a hydrogen atom or $C_{1-6}$ alkyl group (preferably methyl group); and $R^7$ is a hydrogen atom or $C_{1-6}$ alkyl group (preferably methyl group).

Any of the above-described preferred hydroxy amine compounds can be produced by the reductive reaction from nitroxide compounds which are used as free radical spin-labeling agents. These hydroxy amine compounds can trap phenoxy radicals and produce stable radical species. These compounds can be easily prepared by methods described in papers with or without appropriate modifications to the starting materials or reagents used in the methods described in the papers. Furthermore, 4-hydrazomethyl-1-hydroxy-2, 2,5,5-tetramethyl-3-imidazoline-3-oxide (HHTIO) is commercially available (Aldrich Corporation, Code No. 33, 114–7). If necessary, the compounds can be refined or diluted in using them.

A mild reducing agent such as ascorbic acid can be used to reduce a nitroxide compound which is a raw material compound. According to the used method of reduction, the hydroxy amino group may be further reduced and changed into a compound (RR'NH) having an amino group. Since this amino compound is not detected by ESR spectroscopy, if a small amount of such amino compound is introduced in the novel reagent for detection of peroxidase or hydrogen peroxide, no practical problems take place. Generally, the purity of a hydroxy amine compound can be calibrated by $^1$H-NMR measurements.

In the novel method, two or more of the above-described hydroxy amine compounds may be used in conjunction. Hydroxy amine compounds which can be especially preferably used as reagents for trapping electrons of phenoxy radicals and as reagents used for detection of peroxidase or hydrogen peroxide are given below. It is to be noted, however, that reagents used for detection are not limited to these examples:

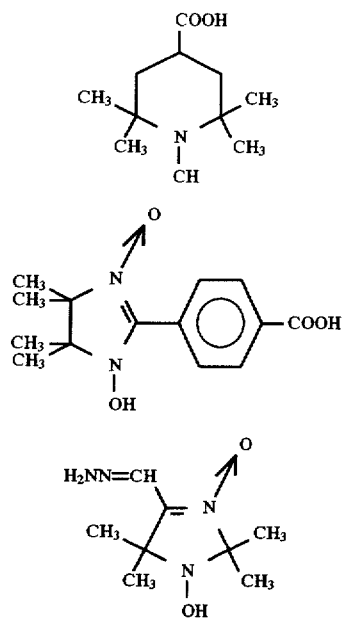

P-substituted phenol compounds which are used in the novel method should be phenol derivative compounds having arbitrary substituted groups at least in the p-position. As decomposition of hydrogen peroxide in the presence of a catalyst consisting of peroxidase progresses, the compound should be readily converted into corresponding phenoxy radicals. As long as these requirements are met, any desired kind of p-substituted phenol compound can be used. In the method according to the present invention, such a p-substituted phenol compound acts as an enhancer in a decomposition reaction of hydrogen peroxide in the presence of peroxidase, or a catalyst. Those skilled in the art can make a decision according to the method described in the body of the present specification as to whether the p-substituted phenol compound has characteristics described above.

The above-described p-substituted phenol compounds may have substituted groups in the m- and/or p-positions. No limitations are imposed on the kind of the substituted group in the p-position existing in the benzene rings of p-substituted phenol compounds or on the kinds of one or more substituted groups not in the p-position. Where two or more substituted groups exist, they may be similar or dissimilar. Examples of these substituted groups include $C_{1-6}$ alkyl group, $C_{1-6}$ alkenyl group, $C_{1-6}$ alkinyl group, $C_{1-6}$ alkoxy group, halogen atoms, halogenated $C_{1-6}$ alkyl group, carboxyl group, carboxy $C_{1-6}$ alkyl group, $C_{1-6}$ alkoxy carbonyl group, hydroxyl group, hydroxy $C_{1-6}$ alkyl group, substituted or non-substituted carbamoyl group, alkyl-substituted or non-substituted amino group, acylamide group, and alkoxylcarbonylamino group.

Alkyl group, alkenyl group, alkinyl group, and alkoxy groups may have either straight chains or branches. Where an unsaturated bond exists, it may be located in any arbitrary position. The halogen atom may be any one of fluorine atom, chlorine atom, bromine atom and iodine atom. Specific examples of the p-substituted phenol compounds include 4-methoxyphenol, 4-ethoxyphenol, 4-iodophenol, 3-(4-hydroxyphenyl) propionic acid (HPPA), 4-hydroxyphenylacetic acid, 4-hydroxyhippuric acid, p-cresol and tyramine.

Examples of p-substituted phenol compounds preferably used in the novel method include the p-substituted phenol compounds given by the above structural formula (2), where $R^1$ is a hydrogen atom or $c_{1-6}$ alkyl group, $R^2$ is $C_{1-6}$ alkyl group, carboxyl, or $C_{1-6}$ alkoxy carbonyl group. Among them, especially preferable compounds include the above-described compounds where $R^1$ is a hydrogen atom and compounds where $R^2$ is $CH_3$, $C_2H_5$, $C_3H_7$, COOH, $OCH_3$ or $OC_2H_5$.

Examples of substances to be detected by the novel method include peroxidase and equivalent catalytic substances such as hemoglobin. Although the measuring method will be described in detail below, the concentrations of reagents, the method of measuring ESR spectra and the ESR spectroscopy are not limited to the illustrated examples. Obviously, appropriate changes and modifications may be made to the illustrated method and apparatus and those skilled in the art can make appropriate choices.

EXAMPLE 1

Production of Reagent for Detection of Peroxidase or Hydrogen Peroxide (1) After dissolving 1 g of carboxy-PTIO [2-(4-carboxyphenyl)-4,4,5,5-tetramethylimidazoline-1-oxyl-3-oxide, 4.99 mmol, produced by Dhojin Chemical Laboratory Inc., Japan] in 5 ml of methanol, ascorbic acid of twice molar quantity was added to the mixture at room temperature. The liquid was stirred until white precipitation appeared. The produced white precipitation was filtered out, cleaned with a small amount of methanol and water and dried. As a result, a reagent of carboxy-PTIOH [2-(4-carboxyphenyl)-4,4,5,5-tetramethylimidazoline-1-N-hydroxy-3-oxide], used for detection of peroxidase or hydrogen peroxide, was obtained.

(2) After dissolving 200 mg of carboxy-TEMPO (4-carboxy-2,2,6,6-tetramethyl-1-piperidinyloxy, 7.21 mmol, prepared by Aldrich Corporation) in 2 ml of methanol, ascorbic acid of twice molar quantity was added to the mixture at room temperature. The liquid was stirred until white precipitation appeared. The produced white precipitation was filtered out, cleaned with a small amount of methanol and water and dried. As a result, a reagent of 4-carboxy-2,2,6,6-tetramethyl-1-N-hydroxypiperidine, used for detection of peroxidase or hydrogen peroxide, was obtained.

EXAMPLE 2

Detection of Peroxidase

As a buffer solution for detection, 0.1M MOPS buffer solution having a pH of 6.5 and containing 0.015% $H_2O_2$ was used. As a substrate compound, p-acetamide phenol (25 mM, aqueous solution) was used. As a hydroxy amine compound that is a reagent used for detection of peroxidase, 50 µg/ml DMSO solution of 4-hydrazonomethyl-1-hydroxy-2,2,5,5-tetramethyl-3-imidazoline-3-oxide (HHTIO) (Aldrich Corporation) or 50 µg/ml DMSO solution of hydroxy amine compound (carboxy-PTIOH) of Example 1 or 2 was used. As an enzyme solution, $10^{-4}$ units/ml of peroxidase solution was prepared with 0.01M DIPSO buffer solution having a pH of 6.5.

Figure 1B:
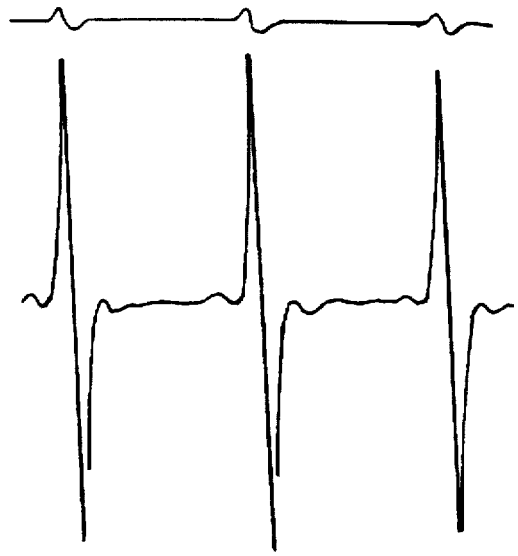
FIG. 1(b) is an ESR spectrum of a hydroxy amine compound, consisting of HHTIO, oxidized by phenoxy radicals, and in which the upper line indicates the ESR signal under a blank condition.

100 µl of the buffer solution for detection, 110 µl of extra pure water, 30 µl of the substrate compound, 10 µl of the hydroxy amine compound, and 50 µl of the enzyme solution are mixed. The mixture was caused to react with each other at room temperature for 15 minutes. The amounts of produced nitroxide radical species were measured by ESR spectroscopy. The results are shown in FIGS. 1(a) and 1(b). FIG. 1(a) shows the results of detection of carboxy-PTIOH. FIG. 1(b) shows the results of detection of HHTIO. The top of signal lines indicates the results of detection of a blank. As can be seen from these results, where the p-substituted phenol was added, the ESR signal intensity was much greater than the signal obtained from the blank to which no peroxidase was added. The ESR measurements were made under the following conditions: the center magnetic field strength was 3346±50 Gauss; modulation was made at 100 kHz and 1.0 Gauss; the power was 20 mW; the gains were 1×100 and 5×10, respectively; and the response was 0.1 sec.

EXAMPLE 3

Detection of Peroxidase, Using P-Hydroxyacetanilide Derivative

P-hydroxyacetanilide derivatives, p-methoxy phenol, p-cresol, thyroxine, and 3-(4-hydroxyphenyl) propionic acid (HPPA) were used as p-substituted phenol derivatives. HHTIO was used as a hydroxy amine compound, which is a detection reagent. Using these compounds, peroxidase was quantitatively detected. As a buffer solution for the detection, 0.1M MOPS buffer solution having a pH of 6.5 and containing 0.015% $H_2O_2$ was used. As a substrate solution, an aqueous solution (25 mM) was used. As an enzyme solution, $10^{-4}$ units/ml of POD solution was adjusted with 0.01M MOPS buffer solution having a pH of 7.0. As an HHTIO solution, 50 µg/ml solution was prepared with DMSO.

50 µl of the POD solution to 100 µl of the buffer solution, 30 µl of the substrate solution, 120 µl of $H_2O_2$, and 10 µl of the HHTIO solution are mixed. The mixture was caused to react with each other at room temperature for 30 minutes. The amounts of the produced radicals were measured with an ESR spectrometer JES-FR80 manufactured by JEOL Ltd., Japan, under the following conditions: the center magnetic field strength was 3346±50 Gauss; modulation was made at 100 kHz and 1.0 Gauss; the power was 20 mW; the gains were 1×100 and 5×10, respectively; and the response was 0.3 sec. The results are listed in Table 1 below. In Table 1, the efficiency of enhancement of the sensitivity is the peak height/blank. It can be seen that the p-hydroxyanilide derivatives showed higher efficiencies of enhancement of the sensitivity than other phenolic compounds.

TABLE 1

| p-substituted phenol | peak height (mm) | efficiency of enhancement of sensitivity |
|---|---|---|
| blank | 3.0 | — |
| $R^1 = H, R^2 = CH_3$ | 610 | 203.3 |
| $R^1 = H, R^2 = C_2H_5$ | 625 | 208.3 |
| $R^1 = H, R^2 = C_3H_7$ | 580 | 193.3 |
| $R^1 = H, R^2 = COOH$ | 60 | 20.0 |
| $R^1 = H, R^2 = OCH_3$ | 710 | 236.8 |
| $R^1 = H, R^2 = OC_2H_5$ | 592 | 197.3 |
| p-methoxyphenol | 405 | 135.0 |
| p-cresol | 125 | 41.7 |
| thyroxine | 10.0 | 3.3 |
| HPPA | 18.0 | 6.0 |

EXAMPLE 4

Comparison of the Novel Method with Prior Art Method, Using Color-Producing Reagents ABTS and OPD The sensitivity of the novel method was compared with the sensitivity of the prior art method, using ABTS [2,2-azino-bis (3-ethyl-benzothiazoline-6-sulfonic) acid] and OPD (o-phenylene diamine) which are typical color-producing reagents used for detection of peroxidase.

For the measurements with ABTS, a substrate buffer solution and a color-producing reagent attached to Lanaenzyme 439 kit manufactured by Nippon Kayaku Co., Ltd., Japan, where used, and 300 µl of the substrate solution whose ABTS concentration was adjusted to 2.5 mg/ml was employed.

For the measurements with OPD, an OPD tablet-dissolving solution attached to HBs antigen-measuring reagent AUSZYME II prepared by Abbot Inc. were used. 5 ml of the OPD tablet-dissolving solution was added per tablet. 300 µl of the substrate solution whose OPD concentration was adjusted to 3 mg/ml was used. 50 µl of peroxidase solution (10–5 u/ml) was added to 300 µl of each substrate solution. Both mixtures were caused to react at room temperature for 30 minutes. For the measurements with ABTS, the reaction was quenched or brought to a stop by adding 1000 µl of $H_2O$.

For the measurements with OPD, 1000 µl of 1N $H_2SO_4$ was added for the same purpose. The final volume of the final product was controlled to 1000 µl. The OD values were measured, using a spectrophotometer U-2000 manufactured by Hitachi Ltd., Japan. Wavelengths of 414 nm and 490 nm, respectively, were used for the measurements, using ABTS and OPD, respectively.

Figure 2A:
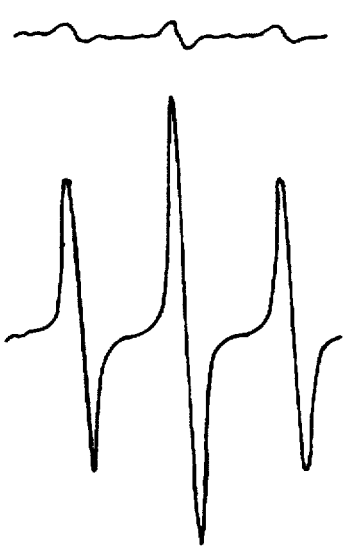
FIG. 2(a) is an ESR spectrum similar to FIG. 1(a), but showing the signal-to-noise ratio (S/N) of a measurement performed by a method according to the invention where the concentration of the peroxidase solution is $10^{-5}$ u/ml.
Figure 2B:
FIG. 2(b) is an ESR spectrum similar to FIG. 1(b), but showing the S/N of a measurement performed by a method according to the invention where the concentration of the peroxidase solution is $10^{-5}$ u/ml.

Measurements by the novel method using hydroxy amine compounds were carried out similarly to the measurements of Example 3 except that the amount of ultra pure water was 160 µl and that the gain was ×200. The results are listed in Table 2. The results of measurements by the novel method are shown in FIGS. 2(a) and 2(b). FIG. 2(a) shows the results of the measurement using carboxy-PTIOH. FIG. 2(b) shows the results of the measurement using HHTIO. The top lines indicate the results of measurements using a blank. The signal-to-noise ratios (S/N) where ABTS and OPD were used were 3.0 and 3.3, respectively. In the novel method, where HHTIO was used, the S/N of the obtained ESR signal was 47.6. Where PTIOH was used, the S/N was 15.3. In this way, the measuring method according to the invention provides much higher sensitivity than the prior art method.

TABLE 2

| specimen | ABTS (414 nm) | OPD (490 nm) | inventive (mm) |
| --- | --- | --- | --- |
| blank | 0.004 | 0.003 | 2.5 |
| POD $10^{-5}$ u/ml | 0.012 | 0.010 | 11 |

EXAMPLE 5

Detection of Hydrogen Peroxide $H_2O_2$

Figure 3:
FIG. 3 is a chart showing ESR signal waveforms obtained by changing the concentration of hydrogen peroxide in Example 5.
Figure 4:
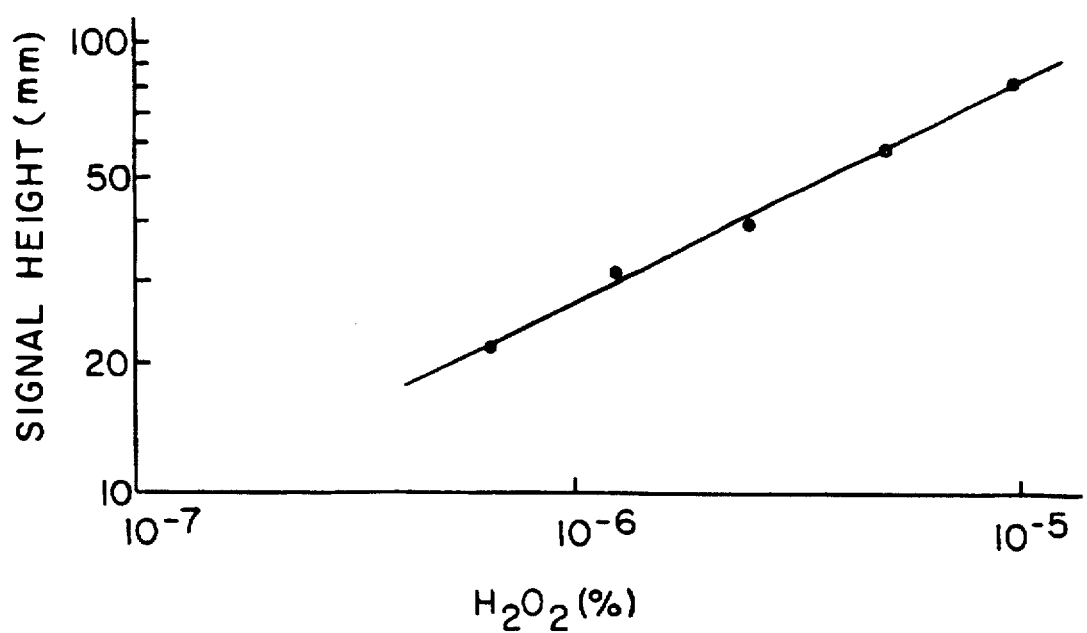
FIG. 4 is a graph showing the relation of the ESR signal intensity to the concentration of hydrogen peroxide obtained in Example 5.

100 μl of DIPSO buffer solution (0.1M, pH: 7.0), 30 μl of p-acetamide phenol (20 mmol/L), 10 μl of HHTIO (1 mmol/L), and 50 μl of peroxidase solution ($10^{-1}$ units/ml) was added to 100 μl of $H_2O_2$ diluted solution (concentration %). They were made to react with each other at room temperature for 10 minutes. Then, the amounts of produced radicals were measured by an ESR spectrometer. The amount of the peroxidase was excessive for $H_2O_2$. Measurements were made with five concentrations of the $H_2O_2$ diluted solution (i.e., $0.625 \times 10^{-6}\%$, $1.25 \times 10^{-6}\%$, $2.5 \times 10^{-6}\%$, $5.0 \times 10^{-6}\%$, and $10 \times 10^{-6}\%$). The results of the measurements are shown in FIGS. 3 and 4. FIG. 3 shows ESR signal waveforms at these various concentrations. FIG. 4 is a graph in which the relation of the concentration to the ESR signal intensity is plotted. As can be seen from FIG. 4, a proportional relation exists between the ESR signal intensity and the concentration of hydrogen peroxide. Detection of hydrogen peroxide at the concentration of $1.25 \times 10^{-6}\%$ was possible. The ESR measurements were made under the following conditions: the center magnetic field strength was 337.500 mT; modulation was made at 100 kHz and 0.1 mT; the power was 10 mW; the gain was ×200; and the response was 0.1 sec.

EXAMPLE 6

Application to Biochemical Tests

Example 5 has demonstrated that quantitative measurement of $H_2O_2$ is possible under a condition that peroxidase is overabundant to $H_2O_2$. There are many biochemical tests based on quantitative measurements of $H_2O_2$ produced by an enzyme reaction. Such tests are directed to measurements of glucose, lactic acid, pyruvic acid, sialic acids, uric acid, creatinine, polyamine, total cholesterol, free cholesterol, neutral fat, phospholipid, free aliphatic acid, inorganic phosphorus, etc. Accordingly, it is possible to adopt the novel method in such tests by quantitatively measuring $H_2O_2$ produced by an enzyme reaction.

As one example of application of the present invention to biochemical tests, a quantitative measurement of glucose is described below.

100 be of MOPS buffer solution (0.1M, pH: 6.5), 50 μl of p-acetamide phenol (20 mmol/L), 1 μl of a standard substance (100, 200 or 400 mg/dL) or monitored sera (Moni-Trol I & II, Baxter Diagnostic Inc.), 10 μl of HHTIO (3 mmol/L), 50 μl of peroxidase solution ($10^{-1}$ units/ml) and 50 μl of glucose oxidase (5/units/ml) were mixed. The mixture was stirred and then caused to react at 37° C. for 10 minutes. A reaction-stopping agent, or 50 μl of $NaN_3$ (500 mmol/L), was added. Thereafter, measurements were made by ESR spectroscopy.

Figure 5A:
FIG. 5(a) is a chart showing ESR signal waveforms derived from a standard substance in Example 6.
Figure 5B:
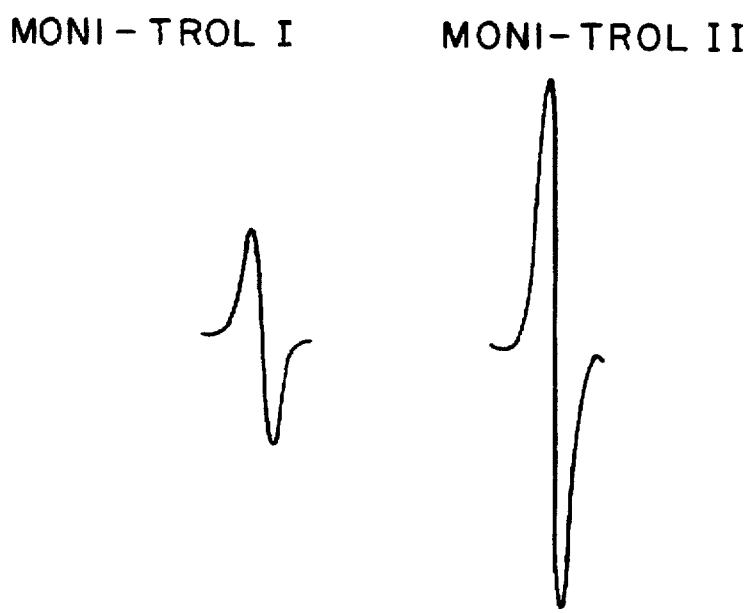
FIG. 5(b) is a chart showing ESR signal waveforms derived from monitored control sera in Example 6.

FIG. 5(a) shows ESR signal waveforms derived from the standard substance. FIG. 5(b) shows ESR signal waveforms obtained from the monitored sera Moni-Trol I & II. The values of the sera Moni-Trol I & II found, based on the standard substance, are 80 mg/dL and 235 mg/dL, respectively, which well agree with the values denoted on the containers of the sera.

According to the present invention, peroxidase or hydrogen peroxide can be detected with high sensitivity. Also, analysis of peroxidase which is so dilute that it cannot be detected by the prior art method is enabled.

Having thus described our invention with the detail and particularity required by the Patent Laws, what is desired protected by Letters Patent is set forth in the following claims.

What is claimed is:

1. A method for detecting peroxidase or hydrogen peroxide, said method comprising the steps of:
   preparing peroxidase and hydrogen peroxide such that one of them is overabundant to the other;
   producing phenoxy radicals from a p-substituted phenol compound by the action of the peroxidase in the presence of the hydrogen peroxide;
   transferring electrons from said phenoxy radicals to a hydroxy amine compound and producing stable radical species of said hydroxy amine compound; and
   measuring electron spin resonances of said stable radical species.

2. The method of claim 1, wherein said p-substituted phenol compound is a 4-acetamide phenol derivative given by

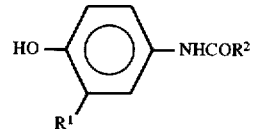

where $R^1$ is a hydrogen atom or $C_{1-6}$ alkyl group, $R^2$ is $C_{1-6}$ alkyl group, carboxyl, or $C_{1-6}$ alkoxy carbonyl group.

3. The method of claim 1, wherein said p-substituted phenol compound is selected from the group consisting of 4-methoxyphenol, 4-ethoxyphenol, 4-iodophenol, 3-(4-hydroxyphenyl) propionic acid, 4-hydroxyphenylacetic acid, 4-hydroxyhippuric acid, p-cresol and tyramine.

4. A reagent for detection of peroxidase or hydrogen peroxide, said reagent consisting of a hydroxy amine compound which can accent electrons transferred from phenoxy radicals to produce stable radical species of said hydroxy amine compound, said phenoxy radicals formed by the action of peroxidase in the presence of hydrogen peroxide and a p-substituted phenol compound.

5. The reagent of claim 4, wherein said p-substituted phenol compound is a 4-acetamide phenol derivative of the formula

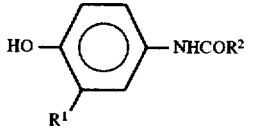

where $R^1$ is a hydrogen atom or $C_{1-6}$ alkyl group, $R^2$ is $C_{1-6}$ alkyl group, carboxyl, or $C_{1-6}$ alkoxy carbonyl group.

6. The reagent of claim 4, wherein said hydroxy amine compound is produced by reducing a nitroxide compound which can be used as a spin-labeling agent for free radicals.

7. A hydroxy amine compound capable of accepting electrons transferred from phenoxy radicals created by the action of peroxidase in the presence of hydrogen peroxide and a p-substituted phenol derivative and which can produce stable radical species of said hydroxy amine compound.

8. The method of claim 1 wherein said hydroxy amine compound is produced by reducing a nitroxide compound which can be used as a spin-labeling agent for free radicals.

* * * * *

UNITED STATES PATENT AND TRADEMARK OFFICE
CERTIFICATE OF CORRECTION

PATENT NO. : 5,780,257
DATED : July 14, 1998
INVENTOR(S) : Masaaki Aoyama et al.

It is certified that error appears in the above-identified patent and that said Letters Patent is hereby corrected as shown below:

Title Page, insert:
   --[30] Foreign Application Priority Data
      Jul. 20, 1995  [JP]  Japan.......7-183869--.

Column 4, first diagram, bottom letters "CH" should read --OH--.

Column 5, first diagram, bottom letters "CH" should read --OH--.

Column 6 Line 26 "$C_{1-6}$" should read --$C_{1-6}$--.

Column 8 Line 24 after "ABTS [2,2" insert --'--.

Column 8 Line 40 "10-5" should read --$10^{-5}$--.

Column 9 Line 51 "100 be of MOPS" should read --100 $\mu$l of MOPS--.

Claim 4 Column 10 Line 39 "accent" should read --accept--.

Signed and Sealed this

Second Day of February, 1999

Attest:

Attesting Officer

*Acting Commissioner of Patents and Trademarks*